US00PP16520P2

(12) United States Plant Patent
Trees

(10) Patent No.: US PP16,520 P2
(45) Date of Patent: May 9, 2006

(54) ***LANTANA* PLANT NAMED 'BALUCPEA'**

(50) Latin Name: *Lantana camara*
Varietal Denomination: Balucpea

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 107 days.

(21) Appl. No.: 11/017,575

(22) Filed: Dec. 20, 2004

(51) Int. Cl.
*A01H 5/00* (2006.01)

(52) U.S. Cl. ..... Plt./227

(58) Field of Classification Search ..... Plt./227
See application file for complete search history.

*Primary Examiner*—Kent Bell
(74) *Attorney, Agent, or Firm*—Wood, Phillips, Katz, Clark & Mortimer

(57) ABSTRACT

A new and distinct cultivar of *Lantana* plant named 'Bulucpea' characterized by its flowers transitioning in color from medium yellow when first open to orange at maturity, free flowering, dark green-colored foliage, and compact, upright, and mounded growth habit.

1 Drawing Sheet

Latin name of genus and species of plant claimed: *Lantana camara.*
Variety denomination: 'Balucpea'.

BACKGROUND OF THE INVENTION

The present invention relates to a new and distinct cultivar of *Lantana* plant botanically known as *Lantana camara* and hereinafter referred to by the cultivar name 'Balucpea'.

The new cultivar originated in a controlled breeding program during August 2000, at West Chicago, Ill. The objective of the breeding program was the development of new *Lantana* cultivars with a well-branched and compact habit, continuous flowering, and dark green-colored foliage.

The new cultivar was the product of the open-pollination of the commercially available *Lantana* cultivar Confetti, not patented, characterized by its pink/yellow-colored flowers and vigorous, spreading growth habit. The new cultivar was discovered and selected by the inventor in February 2001 at Arroyo Grande, Calif. as a single flowering plant within the progeny of the above stated open-pollination.

Asexual reproduction of the new cultivar by terminal stem cuttings since February 2001 at Arroyo Grande, Calif. and West Chicago, Ill. has demonstrated that the new cultivar reproduces true to type with all the characteristics, as herein described, firmly fixed and retained through successive generations of such asexual propagation.

SUMMARY OF THE INVENTION

The following charateristics of the new cultivar have been repeatedly observed and can be used to distinguish 'Balucpea' as a new and distinct cultivar of *Lantana* plant:

1. Flower color transitioning from medium yelllow when first open to orange at maturity.
2. Freely flowering.
3. Dark green-colored foliage.
4. Compact, upright, and mounded growth habit.

Plants of the new cultivar differ from plants of the female parent primarily in growth habit and leaf size.

Of the many commercially available *Lantana* cultivars know to the inventor, the most similar to the new cultivar is 'Balucpeach', U.S. Plant Pat. No. 14,637. However, in side-by-side comparisons, plants of the new cultivar differ from plants of 'Balucpeach' in the following characteristics:

1. Plants of the new cultivar have smaller leaves than plants of the 'Balucpeach'.
2. Plants of the new cultivar have flowers of a lighter color than plants of 'Balucpeach'.
3. Plants of the new cultivar have shorter internodes than plants of 'Balucpeach'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balucpea'. The plants were grown for 7 weeks in a greenhouse at West Chicago, Ill.

DETAILED BOTANICAL DESCRIPTION

Figure 1:
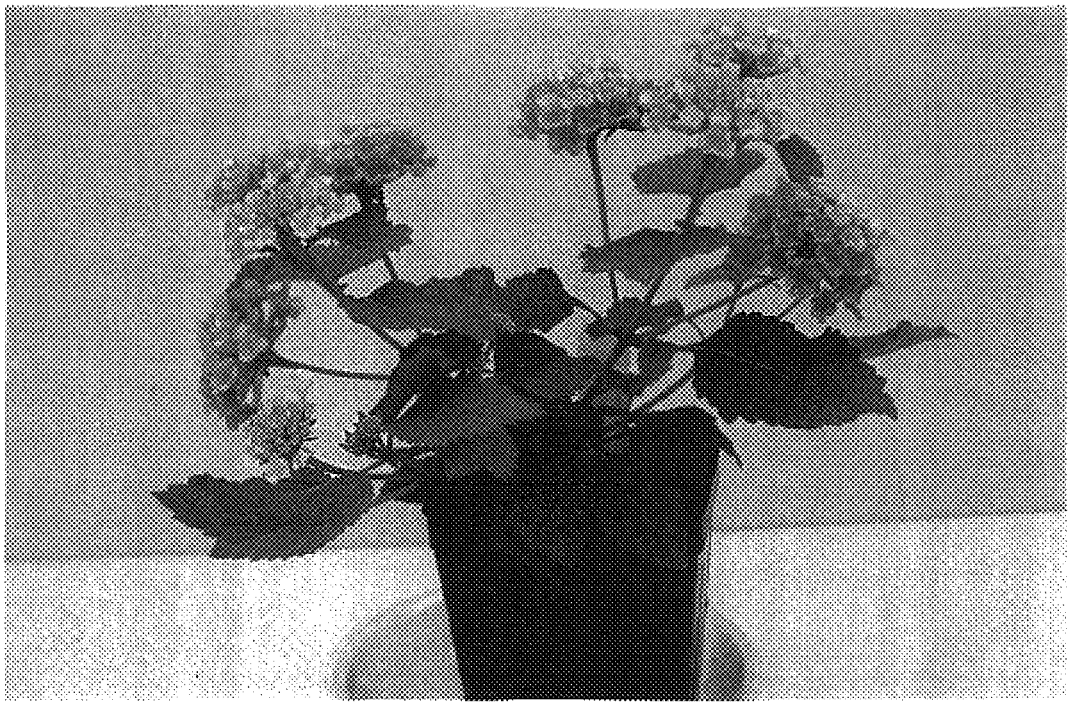
FIG. 1 illustrates a side view of the overall growth and flowering habit of 'Balucpea'.
Figure 2:
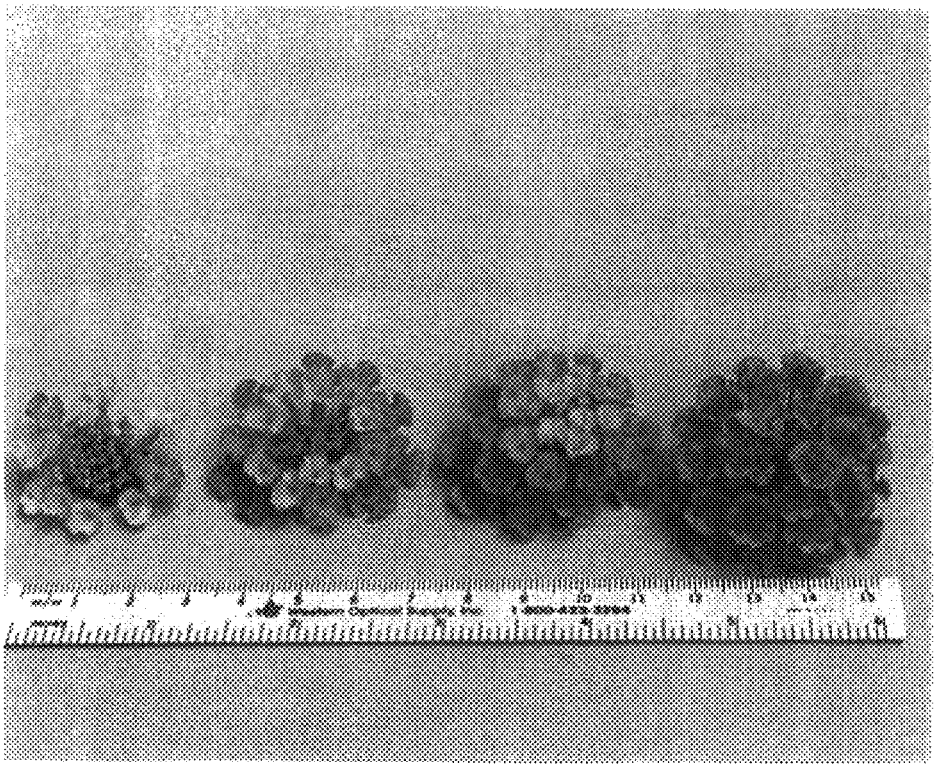
FIG. 2 illustrates a close-up view of a series of inflorescences of 'Balucpea' showing the transition in coloration from first open (at left) to fully mature (at right).

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where general color terms of ordinary significance are used. The color values were determined on Sep. 24, 2004 between 9:00 and 11:00 a.m. under natural light conditions.

The following descriptions and measurements describe plants produced from terminal stem cuttings taken from stock plants and grown in a double polycarbonate-covered greenhouse under conditions comparable to those used in commercial practice. The plants were grown at West Chicago, Ill. in 10 cm pots for 7 weeks using a soilless growth medium. Greenhouse temperatures were maintained at approximately 75°–85° F. (24°–29° C.) during the day and approximately 62°–68° F. (17°–20° C.) during the night. Greenhouse light levels were maintained at 4,000 to 10,000 footcandles during the day.

Botanical classification: *Lantana camara* cultivar Balucpea.

Parentage:

*Female parent.*—Open-pollination of *Lantana* cultivar Confetti, not patented.

Propagation:

*Type cutting.*—Terminal stem cutting.

*Time to initiate roots.*—Approximately 7 to 11 days.

*Time to produce a rooted cutting.*—Approximately 4 weeks.

*Root description.*—Fine, fibrous.

*Rooting habit.*—Freely branching.

Plant description:

*Crop time.*—Approximately 6–7 weeks from a rooted cutting.

*Form.*—Compact, upright, mounded.

*Growth habit.*—Moderately vigorous forming lateral branches at every node. Pinching enhances basal branching.

*Size.*—Height from soil level to top of plant plane: Approximately 16.3 cm. Diameter (area of spread): Approximately 24.1 cm.

*Main branches.*—Quantity: Approximately 4. Shape: Square in cross section. Strength: Strong. Length: Approximately 11.9 cm. Diameter: Approximately 2.9 mm. Texture: Hispid. Color of young supple branch: 144A. Color of mature woody branch: Streaked with 199B and 199C. Internode length at middle of stem: Approximately 2.9 cm.

*Foliage.*—Quantity per lateral branch: Approximately 9. Fragrance: Strong, spicy. Type: Simple. Arrangement: Opposite. Orientation to stem: Obtuse. Shape: Ovate. Margin: Dentate. Apex: Acuminate. Base: Obtuse. Venation pattern: Pinnate. Leaf length: Approximately 6.0 cm. Leaf width: Approximately 4.0 cm. Texture of upper surface: Hispid. Texture of lower surface: Hispid. Color of upper surface of mature foliage: Closest to 139A with veins of 145B. Color of lower surface of mature foliage: 137C with veins of 145C. Petiole length: Approximately 1.3 cm. Petiole diameter: Approximately 1.9 mm. Petiole texture of both surfaces: Moderately covered with short, stiff hairs. Petiole color of both surfaces: Closest to 145C.

Flowering description:

*Flowering habit.*—Freely flowering under outdoor growing conditions with substantially continuous blooming from spring through autumn and year round in greenhouse environment.

*Time to first flower.*—Three weeks after potting a rooted cutting.

Inflorescence description:

*Type.*—Corymb, (Bloom cluster).

*Shape.*—Spherical.

*Quantity per plant.*—Approximately 6 open at any one time.

*Size.*—Depth (height): Approximately 2.6 cm. Diameter: Approximately 4.1 cm. Number of flowers per inflorescence: Approximately 30 fully opened flowers at any one time. Each flower is subtended by a single bract.

*Bract.*—Shape: Lanceolate. Length: Approximately 4.2 mm. Width: Approximately 1.4 mm. Apex: Cuspidate. Base: Truncate. Margin: Entire. Texture: Lower surface is densely pubescent, upper surface is slightly pubescent with short hairs. Color of both surfaces: 137A at tip, gradually transitioning to 144C at base.

Flower description:

*Type/habit.*—Salverform, self-cleaning.

*Fragrance.*—Light, sweet.

*Aspect.*—Upward, outward.

*Lastingness of bloom.*—Approximately 5–7 days from full maturity.

*Bud.*—Buds open in progression from the margin to the center of the inflorescence. Shape: Roughly rectangular. Length: Approximately 4.2 mm. Width: Approximately 2.5 mm. Color: Between 55B and 55C.

*Corolla.*—Form: Five non imbricate, non-symmetrical petals. Length: Approximately 1.0 cm. Width: Approximately 0.9 cm. Petals fused at base forming corolla tube. Texture of upper and lower surfaces of all petals: Glabrous. Color of petals when first open: Upper surface: 9D with 9A around tube opening. Lower surface: 4C. Color of upper surface of petals when fully open: 24D with overlay of 35D at margin and 21A around tube opening of upper petals, 186B at margins of lateral petals. Color of upper surface of lateral petals when fully open: 24D with overlay of 185A and 21A around tube opening. Color of lower surface of lateral petals: Lighter than 155D. Color of all petals when fully mature: Upper surface: 28B and 158D around tube opening. Lower surface: 54A.

*Upper petal.*—Shape: Obovate. Apex: Obtuse. Margin: Entire, ruffled. Length from throat: Approximately 5.7 mm. Width: Approximately 6.5 mm.

*Lateral petals.*—Shape: Obovate. Apex: Obtuse. Margin: Entire. Length from throat: approximately 3.9 mm. Width: Approximately 3.9 mm.

*Lower petal.*—Margin: Entire, ruffled. Length from throat: Approximately 3.7 mm. Width: Approximately 7.2 mm.

*Corolla tube.*—Length: Approximately 1.3 cm. Diameter at tube opening: Approximately 1.4 mm. Diameter at base: Approximately 1.3 mm. Texture of outer surface: Pubescent. Texture of inner surface: Glabrous except for hairs around tube opening. Color of outer surface: 51C at distil end, 29C at proximal end. Color of inner surface: 29C.

*Calyx.*—Shape: Tubular. Composed of 5 sepals fused at base. Length: Approximately 2.3 mm. Diameter: Approximately 1.9 mm. Sepal shape: Lanceolate. Sepal apex: Acute. Sepal length: Approximately 4 mm. Sepal width: Approximately 1 mm. Sepal texture: Outer/lower surface: Dense pubescence. Inner/upper: Glabrous. Color: 145C.

*Peduncle.*—Shape: Tetrahedral. Strength: Strong. Length: Approximately 3.7 cm. Diameter: Approximately 1.4 mm. Angle to stem: 45 degrees. Strength: Strong. Texture: Strigose. Color: 146C.

*Reproductive organs.*—Stamen quantity: Four per flower, adnate to the corolla tube. Filament length:

0.5 mm. Filament color: 2B. Anther shape: Bi-lobed, heart. Anther length: 0.5 mm. Anther color: 163B. Amount of pollen: Moderate. Pollen color: 2D. Pistil quantity: One per flower. Pistil length: 4.2 mm. Stigma shape: Oval. Stigma length: 0.3 mm. Stigma color: 154B. Style length: Approximately 2.9 mm. Style color: 178A. Ovary length: 1 mm. Ovary color: N144C.

*Fruit*.—Classification: Drupe. Shape: Spherical. Diameter: 5 mm. Texture: Glabrous. Color of immature fruit: 144A. Color of mature fruit: Closest to N186B.

*Seed*.—Quantity: Sparse. Diameter: Approximately 4 mm. Color: Closest to 200A.

Disease and pest resistance: Resistance to pathogens or pests common to *Lantana* has not been observed.

What is claimed is:

1. A new and distinct cultivar of *Lantana camara* plant named 'Balucpea', substantially as herein shown and described.

* * * * *